United States Patent
Ko et al.

(10) Patent No.: US 11,774,405 B2
(45) Date of Patent: Oct. 3, 2023

(54) MOBILE DEVICE FOR MEASURING RADON IN GROUNDWATER

(71) Applicant: FTLAB CO., LTD., Ansan-si (KR)

(72) Inventors: Jae Jun Ko, Seoul (KR); Young Gweon Kim, Anyang-si (KR); Yong Jin Seo, Ansan-si (KR); Min Jae Maeng, Suwon-si (KR)

(73) Assignee: FTLAB CO., LTD., Ansan-si (KR)

( * ) Notice: Subject to any disclaimer, the term of this patent is extended or adjusted under 35 U.S.C. 154(b) by 338 days.

(21) Appl. No.: 17/310,028

(22) PCT Filed: Sep. 21, 2020

(86) PCT No.: PCT/KR2020/012682
§ 371 (c)(1),
(2) Date: Jul. 12, 2021

(87) PCT Pub. No.: WO2021/132850
PCT Pub. Date: Jul. 1, 2021

(65) Prior Publication Data
US 2022/0099628 A1 Mar. 31, 2022

(30) Foreign Application Priority Data
Dec. 27, 2019 (KR) .................... 10-2019-0176673

(51) Int. Cl.
*G01N 27/64* (2006.01)
*G01N 1/14* (2006.01)
*G01N 33/18* (2006.01)

(52) U.S. Cl.
CPC .............. *G01N 27/64* (2013.01); *G01N 1/14* (2013.01); *G01N 33/18* (2013.01)

(58) Field of Classification Search
CPC .......... G01N 27/64; G01N 33/18; G01T 7/02; G01T 7/12
See application file for complete search history.

(56) References Cited

U.S. PATENT DOCUMENTS

| 7,795,599 B2 * | 9/2010 | Oliver ...................... G01T 7/04 250/473.1 |
| 2015/0212212 A1 * | 7/2015 | Taleyarkhan ............. G01T 1/18 250/335 |
| 2016/0033462 A1 * | 2/2016 | Singer .................... G01N 33/18 702/6 |

FOREIGN PATENT DOCUMENTS

| JP | 2003-194945 A | 7/2003 |
| KR | 10-1194317 B1 | 10/2012 |
| KR | 10-2015-0072742 A | 6/2015 |
| KR | 10-1672846 B1 | 11/2016 |

(Continued)

OTHER PUBLICATIONS

International Search Report for International application No. PCT/KR2020/012682, dated Nov. 24, 2020, ISA/KR.

*Primary Examiner* — Dominic E Hawkins
(74) *Attorney, Agent, or Firm* — ArentFox Schiff LLP (57) ABSTRACT

A mobile device for measuring radon in groundwater is proposed. The mobile device for measuring radon in groundwater has an effect in that the mobile device enables a user to achieve the same level of reliability as the conventional technology, a previously applied separate dehumidifying device is not required in measuring the radon concentration in groundwater, and while moving from site to site, the user is able to quickly measure the radon concentration in groundwater by the mobile device with a simple configuration and low cost.

13 Claims, 3 Drawing Sheets

(56) References Cited

FOREIGN PATENT DOCUMENTS

| KR | 10-1995927 | B1 | 7/2019 |
| KR | 10-2135694 | B1 | 7/2020 |

\* cited by examiner

Fig 1

MOBILE DEVICE FOR MEASURING RADON IN GROUNDWATER

CROSS-REFERENCE TO RELATED APPLICATION

This application is a 371 U.S. national stage of PCT/KR2020/012682, filed Sep. 21, 2020 which claims the benefit of Korean Patent Application No. 10-2019-0176673, filed Dec. 27, 2019, the contents of each of which are incorporated herein by reference.

TECHNICAL FIELD

The present invention relates to a mobile device for measuring radon in groundwater and, more particularly, to a mobile device that has a simple configuration to which no separate dehumidification device is previously applied and enables a user to easily and directly measure a radon concentration while moving from site to site.

BACKGROUND ART

In general, radon (Rn) is a kind of radioactive gas that has an alpha decay with a half-life of 3.8 days, and is colorless, odorless, and inert. Radon mainly enters a room through cracks in a building from the ground of a floor of the building, and is also generated from decay of uranium contained in cement and soil used in building construction, and other interior and exterior materials, thereby entering the room.

When such radon enters the lungs through the respiratory organs, the radon kills the cells in the lungs and causes cancer, so the World Health Organization (WHO) and the U.S. Environmental Protection Agency (USEPA) define radon as the second major causative agent of lung cancer after smoking and recommend controlling the radon concentration in indoor air. Radon is present in outdoor air or groundwater, but indoor air accounts for about 95% of radon exposure.

That is, since radon is the heaviest gas on earth, once radon enters a room, radon is not well discharged, but accumulates in the room, and through human breathing, radon enters the lungs and decays in the lungs, thereby releasing alpha radiation. The alpha radiation consists of the nucleus of helium (He2+) and has weaker penetration power than that of beta or gamma radiation, but the relatively large mass of radon causes destruction of the lung cells.

An objective of radon management is to reduce the incidence of lung cancer caused by exposure to radon radiation. Radon diffuses from rocks and soil, which contain uranium minerals, and groundwater in which uranium elements are dissolved as free ions, and reaches the surface environment, thereby adversely affecting our human living environment.

Therefore, in order to reduce the harm due to radon, a technique for measuring radon has been developed, which is as follows.

That is, the existing methods of measuring radon in groundwater include: first, a liquid scintillation counting method that has high precision but requires an expensive and complex pretreatment process; second, a time-integrated method that is inexpensive, does not use electricity, but takes a long measurement time of more than a day so as not to allow a user to read an immediate result in a field site; and third, a gas emission method in which a collected groundwater sample is put into a flask, connected to a radon measuring chamber in a closed circulation type by using a dehumidifying device, and then bubbled to measure the concentration of radon discharged into a closed space.

Meanwhile, a radon measurement device using the gas emission method has an inconvenience in that a separate dehumidifying device should be replaced for each time of use and the dehumidifying device and flask should be installed by using a separate stand outside the radon measurement device.

DISCLOSURE

Technical Problem

The present invention is devised to solve the above-described problems, and an objective of the present invention is to provide a mobile device for measuring radon in groundwater, wherein the mobile device enables a user to achieve the same level of reliability as the conventional technology, a previously applied separate dehumidifying device is not required in measuring the radon concentration in groundwater, and while moving from site to site, the user is able to quickly measure the radon concentration in groundwater by the mobile device with a simple configuration and low cost.

Technical Solution

In order to achieve the above-described objective, an aspect of the present invention is to provide a mobile device for measuring radon in groundwater, the mobile device including: a main body provided to be movable by a user and constituting an overall body; a groundwater sample chamber provided inside and outside the main body and storing a water sample collected from the groundwater; an air pump provided inside the main body, and configured to inject air into the water sample stored in the groundwater sample chamber at a constant pressure, and generating air bubbles; a buffer chamber provided inside the main body and configured to temporarily store the air bubbled by the air pump; a radon measurement part provided inside the main body, and configured to suction the air temporarily stored in the buffer chamber, detect in real time alpha particles present in the buffer chamber, output a predetermined alpha particle detection signal, count for a measurement time preset based on the output alpha particle detection signal, and calculate a radon concentration measurement value; a display provided to be exposed to an outer surface of the main body and configured to display the radon concentration measurement value calculated from the radon measurement part on a display screen; and a control part provided inside the main body, and configured to control an operation of the air pump, the buffer chamber, and the radon measurement part so that the air bubbled by the air pump is moved to the radon measurement part via the buffer chamber, and configured to control an operation of the display so as to quantify the radon concentration measurement value calculated from the radon measurement part and display the radon concentration measurement value on the display screen.

Here, the mobile device may further include a communication part configured to wirelessly transmit a current radon concentration measurement value calculated from the radon measurement part.

Preferably, the control part may control an operation of the communication part so that the current radon concentration measurement value calculated from the radon measurement part is transmitted to an external terminal in real time.

Preferably, the external terminal may receive the current radon concentration measurement value transmitted in real time from the communication part through a specific pre-installed application service, and display the current radon concentration measurement value on the display screen so as to allow the user to visually check, in real time, the current radon concentration measurement on the basis of the received current radon concentration measurement value.

Preferably, the external terminal may collect the current radon concentration measurement value, transmitted in real time from the radon measurement part during a preset measurement period, through the pre-installed specific application services, calculate and quantify an average value of the collected radon concentration measurement values, and display the average value on the display screen.

Preferably, the external terminal may convert the current radon concentration measurement value transmitted in real time from the radon measurement part and/or a quantified radon concentration average value through the pre-installed specific application services into a database (DB) for each groundwater sample so as to be stored and managed therein.

Preferably, through the pre-installed specific application services, the external terminal may generate a preset warning message of a radon risk according to the current radon concentration measurement value and/or a quantified radon concentration average value and display the preset warning message on the display screen, when the corresponding current radon concentration measurement value transmitted in real time from the radon measurement part and/or the quantified radon concentration average value exceed a preset risk threshold value of radon concentration.

Preferably, the control part may collect the current radon concentration measurement value transmitted in real time from the radon measurement part during the preset measurement period, calculate and quantify an average value of the collected radon concentration measurement values, and control the operation of the display so as to display the average value on the display screen.

Preferably, the mobile device may further include a storage configured to store the current radon concentration measurement value transmitted in real time from the radon measurement part and a quantified radon concentration average value.

Preferably, the control part may control to convert the current radon concentration measurement value transmitted in real time from the radon measurement part and/or the quantified radon concentration average value into a database (DB) for each groundwater sample, so as to be stored and managed in the storage.

Preferably, the buffer chamber may be provided with a plurality of partitions installed therein for increasing an inner surface area in order to maintain moisture in the air bubbled by the air pump at a constant humidity.

Preferably, the radon measurement part may include at least one radon measurement sensor using an ionization chamber method, and an internal capacity of the buffer chamber may be provided in a range of 1.5 to 2 times larger than an internal capacity of the ionization chamber provided in the radon measuring part.

Advantageous Effects

According to a mobile device for measuring radon in groundwater of the present invention as described above, there is an advantage in that the mobile device enables a user to achieve the same level of reliability as the conventional technology, a previously applied separate dehumidifying device is not required in measuring radon concentration in groundwater, and while moving from site to site, the user is able to quickly the measure radon concentration in groundwater by the mobile device with a simple configuration and low cost.

BEST MODE

The above-described objectives, features, and advantages will be described later in detail with reference to the accompanying drawings, and accordingly, those skilled in the art to which the present invention pertains will be able to easily implement the technical idea of the present invention. In addition, in describing the present disclosure, when it is determined that a detailed description of a known technology related to the present disclosure may unnecessarily obscure the subject matter of the present disclosure, the detailed description thereof will be omitted.

It will be understood that, although the terms including ordinal numbers, such as first, second, etc. may be used herein to describe various elements, these elements should not be limited by these terms. These terms are only used for the purpose of distinguishing one element from another element. For example, the first component may be referred to as a second component without departing from the scope of the present disclosure, and similarly, the second component may be referred to as a first component. The terminology used herein is for the purpose of describing particular exemplary embodiments only and is not intended to be limiting. As used herein, the singular forms are intended to include the plural forms as well, unless the context clearly indicates otherwise.

The terms used in the present disclosure have selected general terms that are currently widely used as possible while considering functions in the embodiments of the present disclosure, but this may vary according to the intention of a technician working in the field, the judicial precedent, the emergence of new technologies, etc. In addition, in certain cases, there are terms arbitrarily selected by the applicant, and in this case, the meaning of the terms will be described in detail in the description of the corresponding embodiments of the present disclosure. Therefore, the terms used in the present disclosure should be defined based on the meaning of the terms and the overall contents of the present disclosure, not simple names of the terms.

Throughout the description of the present invention, when a part is said to "include" or "comprise" a certain component, it means that it may further include or comprise other components, except to exclude other components unless the context clearly indicates otherwise. In addition, terms such as ". . . part" and ". . . module" described in the specification mean parts that process at least one function or operation, which may be implemented as hardware or software, or a combination of hardware and software.

Hereinafter, an exemplary embodiment of the present disclosure will be described in detail with reference to the accompanying drawings. It should be understood that the exemplary embodiment of the present invention may be changed to a variety of embodiments and the scope and spirit of the present invention are not limited to the exemplary embodiment described hereinafter. The embodiments of the present invention are provided to more completely describe the present invention to those skilled in the art.

Combinations of each block of an attached block diagram and each step of the flowchart may be performed by computer program instructions (i.e., execution engine), and since these computer program instructions can be loaded on a processor of a general purpose computer, special purpose computer, or other programmable data processing equipment, the instructions, executed by the processor of the computer or other programmable data processing equipment, will produce means for performing the functions described in each block of the attached block diagram or each step of the flowchart. In order to implement functionality in a specific way, these computer program instructions may also be stored in a computer usable or computer readable memory capable of supporting a computer or other programmable data processing equipment, so that the instructions stored in the computer usable or computer readable memory are able to produce articles of manufacture containing an instruction means for performing functions described in each block in the block diagram or in each step in the flowchart.

In addition, since the computer program instructions may be loaded on the computer or other programmable data processing equipment, a series of operational steps are performed on the computer or other programmable data processing equipment to generate a computer-executed process, so that it is also possible for instructions executing the computer or other programmable data processing equipment to provide steps for executing the functions described in each block of the block diagram and each step of the flowchart.

In addition, it should be noted that each block or each step may represent a module, segment, or part of code that contains one or more executable instructions for executing specified logical functions, and in some alternative embodiments, it is also possible for the functions mentioned in the blocks or steps to be performed out of order. For example, two blocks or steps shown in succession may in fact be performed substantially simultaneously, and the blocks or steps may be performed in the reverse order of the corresponding functions as necessary.

First, a mobile device for measuring radon in groundwater according to an exemplary embodiment of the present invention is configured by applying a gas emission method, which is one of methods for measuring radon in existing groundwater.

Figure 1:
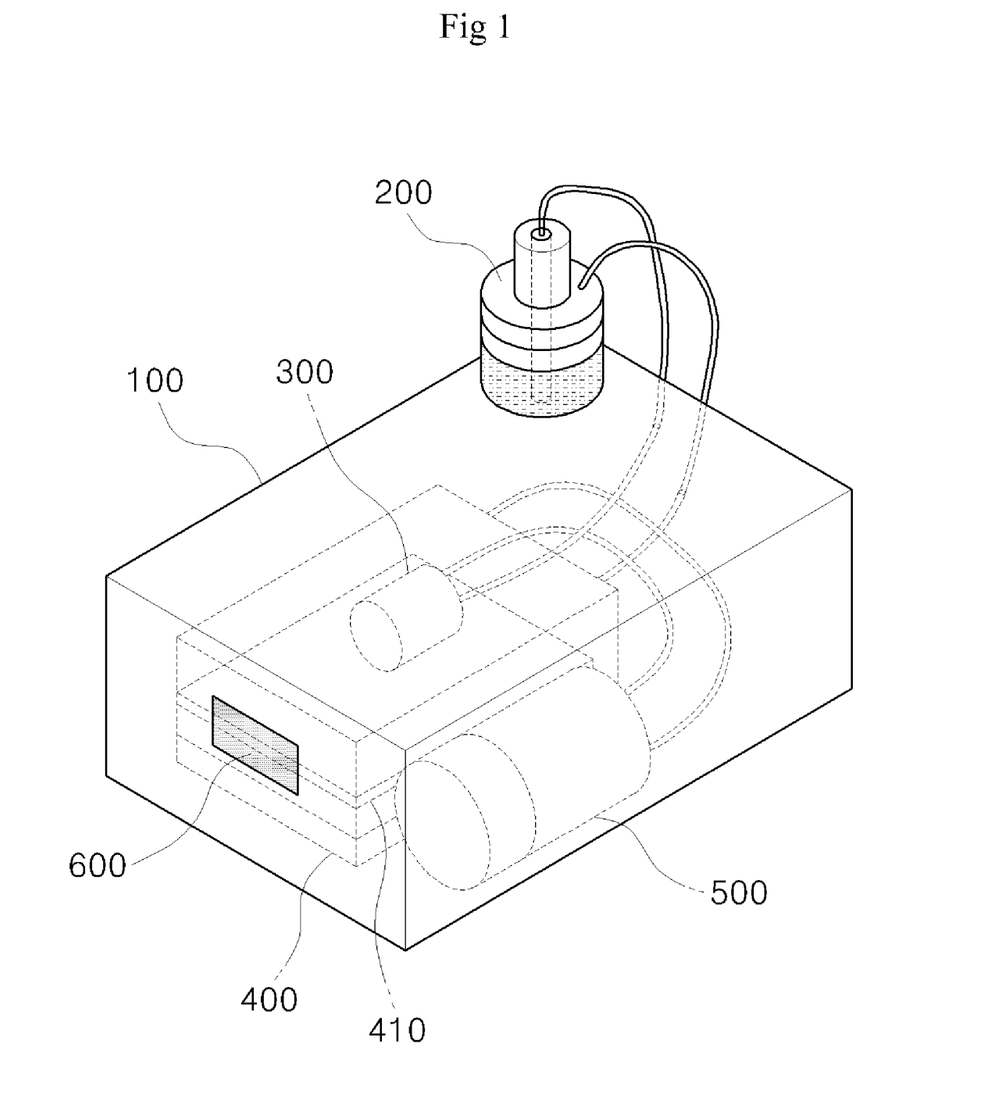
FIG. 1 is a perspective view for illustrating a mobile device for measuring radon in groundwater according to an exemplary embodiment of the present invention.
Figure 2:
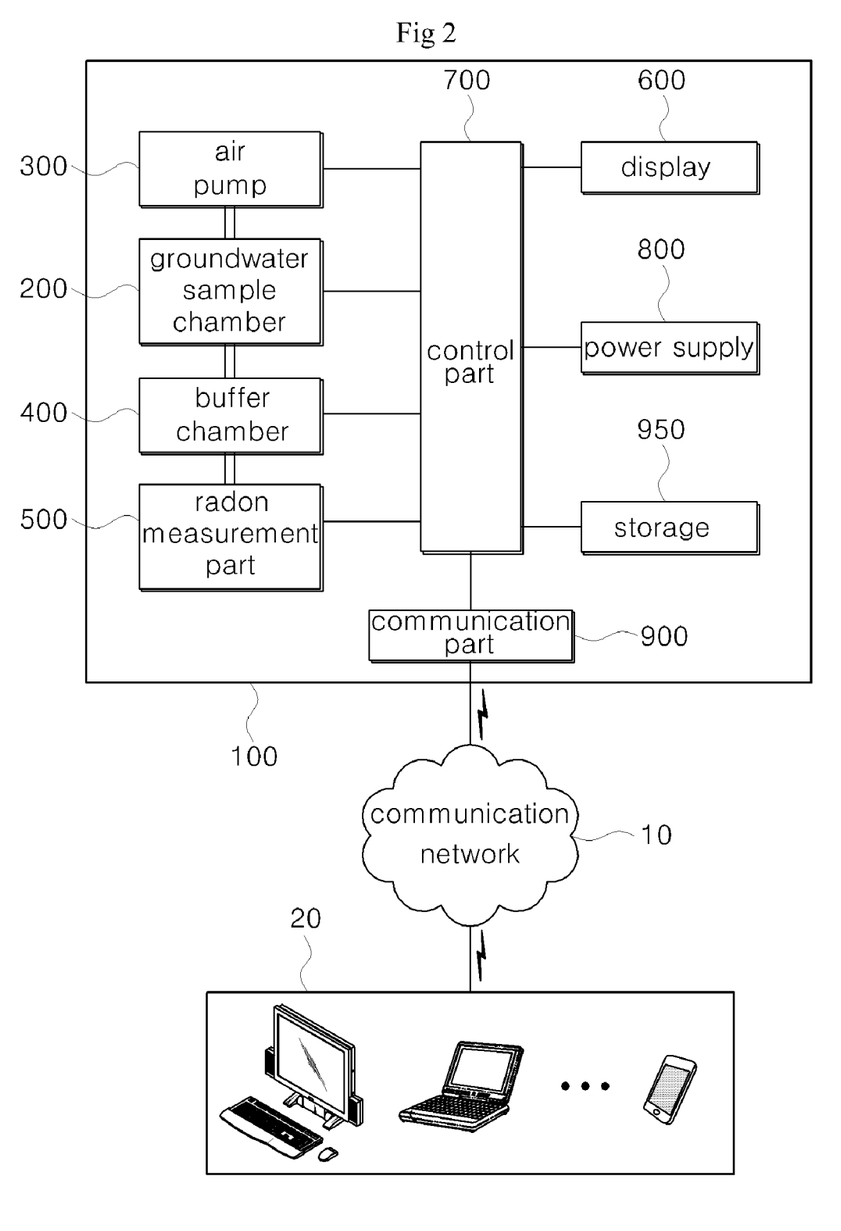
FIG. 2 is an overall block diagram for illustrating the mobile device for measuring radon in groundwater according to the exemplary embodiment of the present invention.
Figure 3:
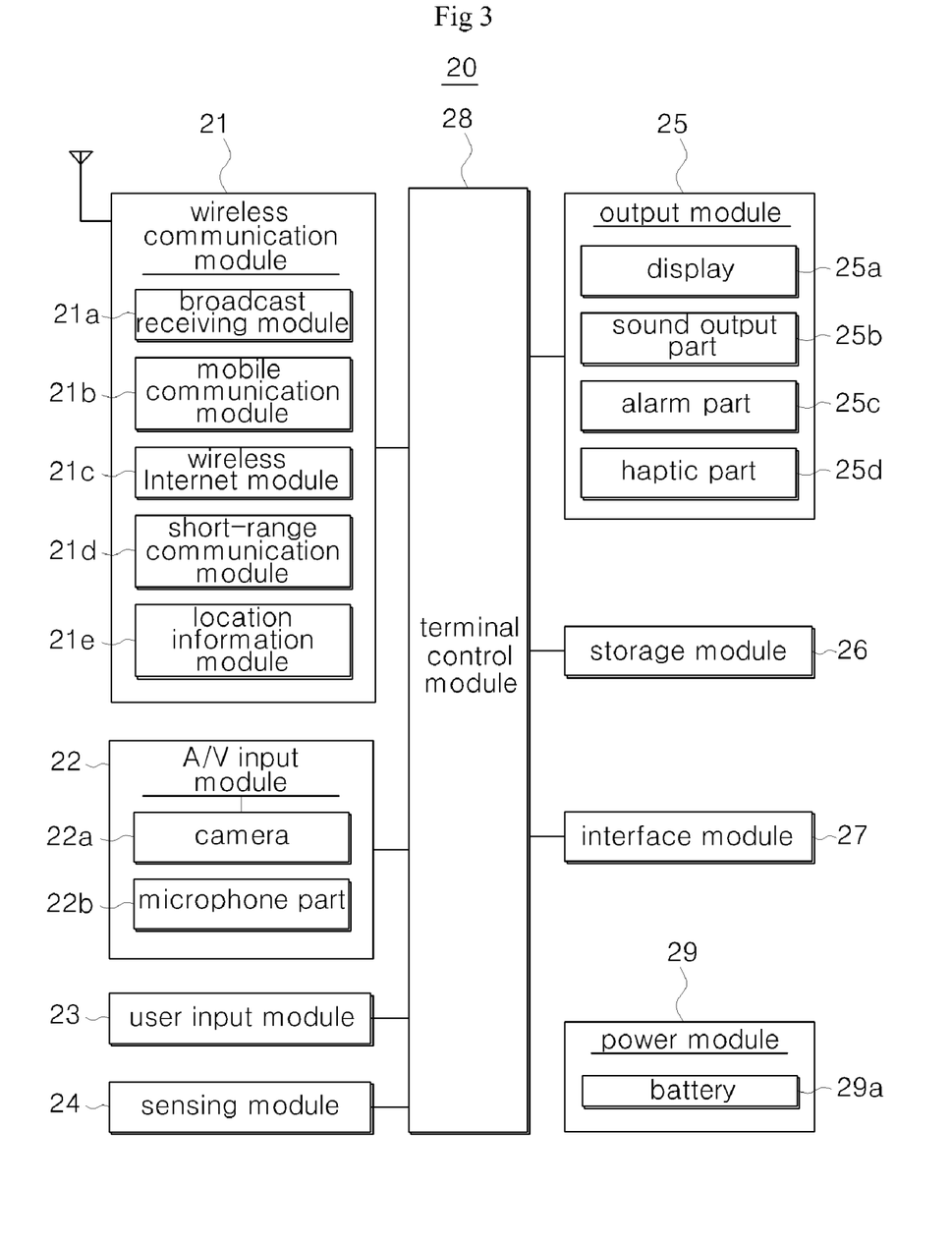
FIG. 3 is a detailed block diagram for illustrating an external terminal applied to the exemplary embodiment of the present invention.

FIG. 1 is a perspective view for illustrating a mobile device for measuring radon in groundwater according to an exemplary embodiment of the present invention, FIG. 2 is an overall block diagram for illustrating the mobile device for measuring radon in groundwater according to the exemplary embodiment of the present invention, and FIG. 3 is a detailed block diagram for illustrating an external terminal applied to the exemplary embodiment of the present invention.

Referring to FIGS. 1 to 3, the mobile device for measuring radon in groundwater according to the exemplary embodiment of the present invention mainly includes: a main body 100, a groundwater sample chamber 200, an air pump 300, a buffer chamber 400, a radon measurement part 500, a display 600, a control part 700, a power supply 800, etc. In addition, the mobile device for measuring radon in groundwater according to the exemplary embodiment of the present invention may further include a communication part 900, a storage 950, an external terminal 20, etc. Meanwhile, since the components shown in FIGS. 1 to 3 are not essential, the mobile device for measuring radon in groundwater according to the exemplary embodiment of the present invention may have more components or fewer components than the components shown in FIGS. 1 to 3.

Hereinafter, the components of the mobile device for measuring radon in groundwater according to the exemplary embodiment of the present invention will be described in detail.

The main body 100 forms an overall outer body in a rectangular box shape, and is provided to be movable by a user. Although not shown in the drawings, it is preferable that, for example, a handle, a wheel, and the like are mounted on an outer surface of the main body 100 so as to be easily moved by the user's hand.

The groundwater sample chamber 200 is provided inside and/or outside the main body 100 and performs a function of storing a water sample collected from groundwater.

Meanwhile, in the exemplary embodiment of the present invention, the groundwater sample chamber 200 is fixedly installed so as to protrude from the outer side of the main body 100, but is not limited thereto and may also be implemented to be fixedly installed or detachable to an inner side of the main body 100.

The air pump 300 is provided inside the main body 100, and performs a function of bubbling so that air bubbles are generated by injecting air, at a predetermined pressure, into the water sample stored in the groundwater sample chamber 200.

The buffer chamber 400 is provided inside the main body 100 and performs a function of temporarily storing the air bubbled by the air pump 300.

In addition, it is preferable that a plurality of partitions 410 that increase an inner surface area is further installed in the buffer chamber 400 in order to maintain moisture, in the air bubbled by the air pump 300, at a predetermined humidity.

In addition, the internal capacity of the buffer chamber 400 is provided to be about 1.5 times or more (i.e., preferably in the range of about 1.5 to 2 times) than the internal capacity of an ionization chamber provided in the radon measurement part 500, so that the humidity is lowered to less than about 40%, which is an appropriate humidity, whereby the influence of humidity may be minimized when measuring radon. For example, when using a 200 cc ionization chamber as a radon measurement sensor, it is preferable for the buffer chamber 400 to have an internal capacity thereof configured to be 300 cc for suitable use.

The radon measurement part 500 is provided inside the main body 100, and performs a function, including: suctioning air temporarily stored in the buffer chamber 400; detecting, in real time, alpha particles present in the buffer chamber 400; outputting a predetermined alpha particle detection signal; counting for a measurement time preset based on the output alpha particle detection signal; and calculating a radon concentration measurement value.

Such a radon measurement part 500 is a sensor for measuring the concentration of radon in groundwater, and for example, it is preferable to use a radon measurement sensor with an ionization chamber type, but is not limited thereto. For example, an alpha particle detector may be applied with a detector such as a surface barrier type detector, a high purity semiconductor detector (i.e., pure Ge detector), a scintillation detector, a solid state junction counter.

That is, the radon measurement sensor with a pulsed ionization chamber type has a structure in which an electrode with a shape of a probe is installed in the center of a cylindrical box made of metal and an electric field is generated by applying a bias voltage between the metal cylindrical box and the probe therein.

When alpha decay occurs inside the ionization chamber and alpha particles are emitted, even though the alpha particles are extinct due to a collision with air, ion charges are generated. Accordingly, when absorbing the ion charges through a central probe and amplifying signals, the alpha particles may be detected. Since the sensor itself is composed of a metal cylinder and a probe, the sensor has an advantage of being very inexpensive, having good durability, and improving ventilation due to the fact that the sensor is not affected by light.

Referring to the surface barrier type detector, due to a surface level or an oxide film, a surface of a semiconductor is formed with a depletion layer such as a PN junction, whereby the vicinity of the surface becomes an obstacle for charge transfer. For practical use, gold is deposited on a surface of n-type Si at about 100 $\mu m/cm^2$, and is used as one electrode, so that radiation is incident on a back surface thereof. Here, the depletion layer has various thicknesses of about 50~500 $\mu m$, and since energy loss at the surface is small, the depletion layer is mainly used for detection of charged particles generated by alpha radiation and has good energy resolution.

The high-purity semiconductor detector is generally referred to as a pure Ge detector. The pure Ge detector is composed of a high-purity Ge crystal having very small impurity concentrations and defects, having a very high electrical resistance at low temperatures, and having a high bias voltage applied thereto as well. The difference between pure Ge and Ge(Li) is that the pure Ge is able to be stored at room temperature, is convenient for maintenance because pure Ge can be used after cooling with liquid nitrogen only when measuring, and has energy resolution that is not inferior to Ge(Li), thereby being put into practical use.

Referring to the scintillation detector, the phenomenon of emitting light when charged particles collide with a substance has been known for a long time, and light emission of NaI coating or zinc sulfide (ZnS) by alpha radiation is particularly strong and is able to be detected and counted with a magnifying glass in a dark room.

Such light emission is called scintillation, and the substance that exhibits this phenomenon is called a scintillator. In addition, the scintillator coupled with a photomultiplier tube is called a scintillation detector, and in particular, a device using a method for counting by a pulse output is called a scintillation counter tube.

Meanwhile, a device using a method of reading an output by direct current is mainly used for dosimetry, and since a scintillator is used, the device is called a scintillation dosimeter. For the scintillator, any solid, liquid, or gas is used, and when liquid is used, the scintillator is called a liquid scintillation counting device.

The solid junction counter is a solid reverse-biased PN junction semiconductor, is a counter configured to collect ionic charges from alpha particles passing through a depletion layer, and may be manufactured in a small, mobile type.

The display 600 is provided to be exposed to the outer surface of the main body 100, and performs a function of displaying a radon concentration measurement value calculated from the radon measurement part 500 on a display screen.

For example, the display 600 may include any one of displays such as Liquid Crystal Display (LCD), Light Emitting Diode (LED), Thin Film Transistor-Liquid Crystal Display (TFT LCD), Organic Light Emitting Diode (OLED), Flexible Display, Plasma Display Panel (PDP), Alternate Lighting of Surfaces (ALiS), Digital Light Processing (DLP), Liquid Crystal on Silicon (LCoS), Surface-conduction Electron-emitter Display (SED), Field Emission Display (FED), Laser TV (quantum dot laser, and liquid-crystal laser), Optoelectronic Liquid Display (FLD), Interferometric Modulator Display (iMoD), Thick-film Dielectric Electroluminescent (TDEL), Quantum Dot-based Light Emitting Display (QD-LED), Telescopic Pixel Display (TPD), Organic Light-emitting Transistor (OLET), Laser-powered Phosphor Display (LPD), 3D display, but is not limited thereto, and any device that can display the radon concentration measurement value may be included.

The control part 700 is provided inside the main body 100 and performs overall control of the mobile device for measuring radon in groundwater according to the exemplary embodiment of the present invention, and in particular, the control part 700 performs a function of controlling an operation of the air pump 300, the buffer chamber 400, and/or the radon measurement part 500, so that the air bubbled by the air pump 300 passes through the buffer chamber 400 and moves to the radon measurement part 500.

In this case, it is preferable for the control part 700 to perform the above-described control function by operating at least one motor, control valve, switch, and the like, which are provided in the air pump 300, the buffer chamber 400, and/or the radon measurement part 500.

In addition, the control part 700 performs a function of controlling the operation of the display 600 so that the radon concentration measurement value calculated from the radon measurement part 500 is numerically displayed on a display screen.

In addition, the control part 700 may perform a function, including: collecting current radon concentration measurement values transmitted in real time from the radon measurement part 500 during a preset measurement period; calculating and quantifying an average value of the collected radon concentration measurement values; and controlling the operation of the display 600, so as to display the average value on the display screen.

In addition, the control part 700 may perform a control function in which a current radon concentration measurement value transmitted in real time from the radon measurement part 500 and/or a quantified radon concentration average value are converted into a database (DB) for each groundwater sample so as to be stored and managed in the storage 950.

In addition, the control part 700 may perform a function of controlling the operation of the communication part 900, so as to transmit in real time the current radon concentration measurement value calculated from the radon measurement part 500 and/or the quantified radon concentration average value to the external terminal 20 through a communication network 10.

In this case, the communication network 10 is a high-speed backbone network of a large communication network capable of providing large-volume, long-distance voice and data services, and may be a next-generation wireless communication network including WiFi, WiGig, Wibro (Wireless Broadband Internet), and Wimax (World Interoperability for Microwave Access), which are for providing Internet or high-speed multimedia services.

The Internet refers to a worldwide open computer network architecture that provides various services present on a TCP/IP protocol and an upper layer of the TCP/IP, the services including: HTTP (Hyper Text Transfer Protocol), Telnet, FTP (File Transfer Protocol), DNS (Domain Name System), SMTP (Simple Mail Transfer Protocol), SNMP (Simple Network Management Protocol), NFS (Network File Service), NIS (Network Information Service), etc. Meanwhile, the Internet may be a wired or wireless Internet, or may be a core network integrated with a wired public network, a wireless mobile communication network, or a mobile Internet.

When provided with a mobile communication network, the communication network 10 may be a synchronous mobile communication network or an asynchronous mobile communication network. A wideband code division multiple access (WCDMA) communication network may be referred to as an exemplary embodiment of the asynchronous mobile communication network. In this case, although not shown in the drawings, the mobile communication network may include, for example, a Radio Network Controller (RNC), etc. Meanwhile, although the WCDMA network is referred to as an example, the communication network 10 may be a next-generation communication network such as a cellular-based 3G network, an LTE network, a 4G network, a 5G network, and other IP-based IP networks. Such a communication network 10 serves to allow the communication part 900 and the external terminal 20 to mutually transmit signals and data therebetween.

In addition, the power supply 800 is provided inside the main body 100 and performs a function of supplying power necessary for each part described above, that is, each part including: the groundwater sample chamber 200, the air pump 300, the buffer chamber 400, the radon measurement part 500, the display 600, the control part 700, the communication part 900, and/or the storage 950. For continuously supplying the power, it is preferable to implement such that a commercial alternating current (AC) power (e.g., AC 220V) is converted into direct current (DC) and/or alternating current (AC) power, but is not limited thereto and the power supply 800 may be implemented by including a conventional portable battery as well.

In addition, the power supply 800 may include a power management part (not shown) that protects components from external power shock and outputs a constant voltage. The power management part may include an electro static damage (ESD) protector, a power detector, a rectifier, a power circuit breaker, etc.

Here, the ESD protector is configured to protect electronic components from static electricity or sudden power shock. The power detector is configured to transmit a blocking signal to the power circuit breaker when a voltage outside the range of allowable voltage is introduced, and transmit a voltage-raising signal or voltage-lowering signal to the rectifier depending on a voltage change within the range of the allowable voltage. The rectifier is configured to perform a voltage-raising or voltage-lowering rectification operation according to a signal from the power detector so that the constant voltage is supplied by minimizing a fluctuation of the input voltage. The power circuit breaker is configured to block the power supplied from the battery according to the blocking signal transmitted from the power detector.

Additionally, the communication part 900 performs a function of wirelessly sending a current radon concentration measurement value calculated from the radon measurement part 500 and/or the quantified radon concentration average value to the external terminal 20 under the control of the control part 700.

Such a communication part 900 is preferably implemented to communicate in a wired and/or wireless method through the communication network 10, but is not limited thereto, and the above wireless communication method may be implemented to use any one of short-range wireless communication including, for example, Bluetooth communication, ZigBee communication, Ultra-Wideband (UWB) communication, Radio Frequency Identification (RFID) communication, or infrared (IR) communication.

In addition, the storage 950 performs a function of storing the current radon concentration measurement value transmitted in real time from the radon measurement part 500 and/or the quantified radon concentration average value under the control of the control part 700.

Such a storage module 950 may include at least one type of storage medium including, for example, a flash memory type, a hard disk type, a multimedia card micro type, a card type memory (e.g., SD or XD memory, etc.), a RAM (Random Access Memory, etc.), a SRAM (Static Random Access Memory), a ROM (Read-Only Memory, ROM), an EEPROM (Electrically Erasable Programmable Read-Only Memory), a PROM (Programmable Read-Only Memory), a magnetic memory, a magnetic disk, and an optical disk.

Various exemplary embodiments described herein may be implemented in a recording medium that can be read by a computer or a similar device by using, for example, software, hardware, or a combination thereof.

According to the hardware implementation, the exemplary embodiment described herein may be implemented by using at least one of electrical parts for performing functions, including: ASICs (application specific integrated circuits), DSPs (digital signal processors), DSPDs (digital signal processing devices), PLDs (programmable logic devices), FPGAs (field programmable gate arrays), processors, controllers, microcontrollers, and microprocessors. In some cases, such exemplary embodiments may be implemented by the control part 700.

According to the software implementation, the exemplary embodiments such as procedures or functions may be implemented together with separate software modules that perform at least one of functions or operations. A software code may be implemented by a software application written in an appropriate programming language. In addition, the software code may be stored in the storage 950 and executed by the control part 700.

In addition, the external terminal 20 may perform a function of receiving a current radon concentration measurement value transmitted in real time from the communication part 900 and/or a quantified radon concentration average value through a specific pre-installed application service, and displaying the values on a display screen so as to allow a user to visually check, in real time, the current radon concentration measurement value and/or the quantified radon concentration average value on the basis of the received values.

In addition, the external terminal 20 may perform a function, including: collecting the current radon concentration measurement value transmitted in real time from the radon measurement part 500 during a preset measurement period through pre-installed specific application services; calculating an average value of the collected radon concentration measurement values; and quantifying the average value to be displayed on a display screen.

In addition, the external terminal 20 may perform a function in which the current radon concentration measurement value transmitted in real time from the radon measurement part 500 and/or the quantified radon concentration average value through the pre-installed specific application services are converted into a database (DB) for each groundwater sample, and are stored and managed therein.

In addition, the external terminal 20 may perform a function of generating a pre-set warning message of radon risk to be displayed on a display screen according to the current radon concentration measurement value and/or the quantified radon concentration average value, in a case where the corresponding current radon concentration measurement value transmitted in real time from the radon measurement part 500 and/or the quantified radon concentration average value through the pre-installed specific application services exceed a preset risk threshold value of radon concentration.

In this case, it is preferable that a risk threshold value of radon concentration corresponding to the current radon concentration measurement value and a risk threshold value of radon concentration corresponding to the quantified radon concentration average value are set with values different from each other.

Meanwhile, the external terminal 20 applied to the exemplary embodiment of the present invention is preferably provided with at least any one of mobile terminal devices, including: a smart phone, a smart pad, or a smart note, which communicate via wireless Internet or mobile Internet. In addition, the external terminal 20 may be collectively referred to all wire/wireless home appliance/communication devices provided with a user interface for connecting to a communication network 10, the devices including a personal PC, a notebook PC, a palm PC, a mobile play-station, a DMB (Digital Multimedia Broadcasting) phone with communication function, a tablet PC, an iPad, etc.

As shown in FIG. 3, such an external terminal 20 may include a wireless communication module 21, an audio/video (A/V) input module 22, a user input module 23, and a sensing module (24), an output module 25, a storage module 26, an interface module 27, a terminal control module 28, a power module 29, etc. Meanwhile, since the components shown in FIG. 3 are not essential, the external terminal 20 may have more components or fewer components than the components shown in FIG. 3.

Hereinafter, a detailed description of the components of the external terminal 20 is as follows.

The wireless communication module 21 may include one or more modules that enable wireless communication between the external terminal 20 and the communication part 505. For example, the wireless communication module 21 may include a broadcast receiving module 21*a*, a mobile communication module 21*b*, a wireless Internet module 21*c*, a short-range communication module 21*d*, a location information module 21*e*, etc.

Through various broadcast channels (e.g., satellite channels, terrestrial channels, etc.), the broadcast receiving module 21*a* receives broadcast signals (e.g., TV broadcast signals, radio broadcast signals, data broadcast signals, and the like) and/or broadcast-related information from an external broadcast management server.

On a mobile communication network, the mobile communication module 21*b* transmits and receives a wireless signal with at least one of a base station, an external terminal 20, and a server. The wireless signal may include a voice call signal, a video call signal, or various types of data according to transmission/reception of text/multimedia messages.

The wireless Internet module 21*c* is a module for accessing the wireless Internet, and may be built in or external to the external terminal 20. As the wireless Internet technology, for example, WLAN (Wi-Fi), Wibro, Wimax, HSDPA, LTE, and the like may be used.

The short-range communication module 21*d* is a module for short-range communication, and for example, Bluetooth communication, ZigBee communication, UWB (Ultra-Wideband) communication, RFID (Radio Frequency Identification) communication, or infrared (IrDA, infrared Data Association) communication, and the like may be used.

The location information module 21*e* is a module for checking or obtaining a location of the external terminal 20, and may obtain current location information of the external terminal 20 by using a Global Position System (GPS), etc.

Meanwhile, according to the control of the terminal control module 28, the above-described wireless communication module 21 and/or a wired communication module (not shown) may perform data transmission/reception with the communication part 900 by using a specific application program stored in the storage module 26.

The A/V input module 22 is a module for inputting an audio signal or a video signal, and may fundamentally include a camera 22*a*, a microphone part 22*b*, etc. The camera 22*a* processes image frames, such as still images or moving pictures, obtained by an image sensor in a video call mode or a photographing mode. The microphone part 22*b* receives an external sound signal by a microphone in a call mode, a recording mode, or a voice recognition mode, and processes the external sound signal as electrical voice data.

The user input module 23 is a module that generates input data for controlling an operation of the external terminal 20, and in particular, performs a function of inputting a selection signal for any one piece of data management information displayed through the display 25*a* of the output module 25. The selection signal may be, for example, a touch panel type input by a user's touch (with a static pressure/electricity type) or may be input by using a separate input device (e.g., a keypad dome switch, a jog wheel, a jog switch, and the like).

The sensing module 24 generates a sensing signal for controlling the operation of the external terminal 20 by detecting a current state of the external terminal 20, the current state being an open/closed state of the external terminal 20, a location of the external terminal 20, presence or absence of user contact, user's action of touching to a specific part, an orientation of the external terminal 20, acceleration/deceleration of the external terminal 20, etc. Such a sensing signal is transmitted to the terminal control module 28, and may serve as a basis where the terminal control module 28 performs a specific function.

The output module 25 is a module for generating an output related to visual, auditory, or tactile sense, and fundamentally, may include a display 25*a*, a sound output part 25*b*, an alarm part 25*c*, and a haptic part 25*d*, and the like.

The display 25*a* is for displaying and outputting information processed by the external terminal 20. For example, when the external terminal 20 is in a call mode, a user interface (UI) or a GUI (Graphical User Interface), which are related to a call, is displayed, and when the external terminal 20 is in a video call mode or a photographing mode, a photographed and/or received image, and UI or GUI are displayed on the display 25*a*.

For example, in a mode including: a call signal reception mode; a call mode or a recording mode; a voice recognition mode; a broadcast reception mode; and the like, the sound output part 25b may output audio data which is stored in the storage module 26 or received from the wireless communication module.

The alarm part 25c may output a signal for notifying the occurrence of an event of the external terminal 20. Examples of events occurring in the external terminal 20 include call signal reception, message reception, key signal input, touch input, etc.

The haptic part 25d generates various tactile effects that a user may feel. A typical example of the tactile effect generated by the haptic part 25d is vibration. The intensity and pattern of the vibration generated by the haptic part 25d may be controlled.

The storage module 26 may store a program for an operation of the terminal control module 28, and may temporarily store input/output data (e.g., data related to a phonebook, a message, a still image, a video, and the like).

In addition, the storage module 26 may store data on numerous vibration and sound of various patterns, which are output when inputting a touch on a touch screen, and may store an application program related to the radon measurement.

In addition, since the storage module 26 may store source data for generating radon measurement-related information, radon measurement-related data may be constructed in a form composed of images and sounds, and a process and a result of generating the radon measurement-related data may also be stored together.

Such a storage module 26 may include at least one type of storage medium, including: a flash memory type storage, a hard disk type storage, a multimedia card micro type storage, a card type memory (e.g., SD or XD memory, etc.), a RAM, a SRAM, a ROM, an EEPROM, a PROM, magnetic memory, a magnetic disk, an optical disc, etc.

The interface module 27 serves as a passage for all external devices connected to the external terminal 20. The interface module 27 receives data transmitted from an external device or power supplied from an external device, so as to transmit the data or power to each component inside the external terminal 20 or transmit the data inside the external terminal 20 to an external device.

The terminal control module 28 generally controls the overall operation of the external terminal 20, and performs controlling and processing related to, for example, a voice call, data communication, a video call, execution of various applications, etc.

That is, the terminal control module 28 performs a control function, so as to control a radon measurement-related application program stored in the storage module 26 to be executed, request generation of radon measurement-related data through execution of the radon measurement-related application program, and receive radon measurement-related data for the above request.

In addition, through the execution of the radon measurement-related application program, the terminal control module 28 performs a control function so that in the process of generating the radon measurement-related data desired by a user, the auxiliary elements including at least one of video, audio, and sound are output to at least one of devices including the display 25a and other output devices (e.g., the sound output part 25b, the alarm part 25c, the haptic part 25d, and the like).

In addition, the terminal control module 28 may monitor the charging current and charging voltage of the battery 29a at all times, and temporarily store the monitored value in the storage module 26. In this case, it is preferable that the storage module 26 stores not only battery charging status information such as the monitored charging current and charging voltage, but also battery specification information (i.e., product code, rating, and the like).

The power module 29 receives external power and internal power applied under the control of the terminal control module 28 to supply the power necessary for the operation of each component. The power module 29 supplies power from the built-in battery 29a to each component to operate, and is capable of charging the battery by using a charging terminal (not shown).

Various exemplary embodiments described herein may be implemented in a recording medium that can be read by a computer or a similar device by using, for example, software, hardware, or a combination thereof.

According to the hardware implementation, the exemplary embodiment described herein may be implemented by using at least one of electrical parts for performing functions, including: ASICs (application specific integrated circuits), DSPs (digital signal processors), DSPDs (digital signal processing devices), PLDs (programmable logic devices), FPGAs (field programmable gate arrays), processors, controllers, microcontrollers, and microprocessors. In some cases, such exemplary embodiments may be implemented by the terminal control module 28.

According to the software implementation, the exemplary embodiments such as procedures or functions may be implemented together with separate software modules that perform at least one of functions or operations. A software code may be implemented by a software application written in an appropriate programming language. In addition, the software code may be stored in the storage module 26 and executed by the terminal control module 28.

Unlike ordinary mobile phones (also known as feature phones), when the external terminal 20 is configured to include a smartphone, the smartphone is to be a phone based on an open operating system that allows users to download, freely use, and delete various application programs they desire. The smartphone is preferably referred to as a communication device that includes: not only all mobile phones provided with mobile office functions, but also functions such as voice/video calls and Internet data communication, which are generally used; or any Internet phone or a tablet PC that does not have a voice call function, but is capable of accessing the Internet.

Such a smartphone may be implemented by applying a smartphone equipped with a variety of open operating systems, and the open operating systems may include, for example, Symbian of NOKIA, Blackberry of RIMS, iOS of Apple, Windows Mobile of Microsoft, Android of Google, Bada of Samsung Electronics, etc.

As described above, since a smartphone uses the open operating system, unlike a mobile phone having a closed operating system, a user is able to arbitrarily install and manage various application programs.

That is, the above-described smartphone fundamentally includes: a control part, a memory, a screen output part, a key input part, a sound output part, a sound input part, a camera, a wireless network communication module, a short-range wireless communication module, a battery for power supply, etc.

The control part is a generic term for referring to a functional component that controls the operation of a smart phone, includes at least one processor and a memory for execution, and is connected to each part of the functional component provided in the smart phone through a bus.

Such an above-described control part loads and operates at least one program code provided in a smartphone through the processor into the memory for execution, and transfers the operation result to at least one part of the functional component through the bus so as to control the operation of the smartphone.

The memory is a generic term for a nonvolatile memory provided in a smartphone, and stores and maintains at least one program code executed through the control part and at least one data set used by the program code. The memory fundamentally stores: a system program code and a system data set corresponding to an operating system of a smartphone; a communication program code and a communication data set for processing wireless communication connection of the smartphone; and at least one application program code and application data set, wherein a program code and a data set for implementing the present invention are stored in the memory as well.

The screen output part is composed of a screen output device (e.g., liquid crystal display (LCD) device) and an output module that drives the screen output device, and is connected to the control part via the bus, thereby outputting an operation result, corresponding to a screen output among various operation results of the control part, on the screen output device.

The key input part is composed of a key input device having at least one key button (or a touch screen device interlocking with the screen output part) and an input module that drives the key input part, and is connected to the control part via the bus, thereby inputting a command that instructs various operations of the control part or inputting data necessary for the operations of the control part.

The sound output part includes: a speaker that outputs a sound signal; and a sound module that drives the speaker, and is connected to the control part via the bus, thereby outputting, through the speaker, an operation result corresponding to a sound output among various operation results of the control part. The sound module decodes sound data to be output through the speaker and converts the sound data into a sound signal.

The sound input part includes: a microphone that receives a sound signal; and a sound module that drives the microphone, and transmits the sound data input through the microphone to the control part. The sound module encodes the sound signal input through the microphone.

The camera includes an optical part, a charge coupled device (CCD), and a camera module for driving the same, and obtains bitmap data input to the CCD through the optical part. The bitmap data may include video data and the image data of a still image.

The wireless network communication module is a generic term for communication components for connecting wireless communication, is configured to include at least one of an antenna, an RF module, a baseband module, and a signal processing module, which are for transmitting and receiving radio frequency signals of a specific frequency band, and is connected to the control part via the bus, thereby transmitting, through wireless communication, an operation result corresponding to wireless communication among various operation results of the control part or receiving data through wireless communication, so as to transmit the data to the control part and simultaneously maintain the procedures of connection, registration, communication, and handoff of the wireless communication.

In addition, the wireless network communication module includes a mobile communication component that performs at least one of functions, including: access to a mobile communication network, location registration, call processing, call connection, data communication, and handoff, in accordance with the CDMA/WCDMA standard. Meanwhile, according to the intention of those skilled in the art, the wireless network communication module according to the IEEE 802.16 standard further include a mobile Internet communication component for performing at least one of functions, including: access to the mobile Internet, location registration, data communication, and handoff, wherein it should be understood that the present invention is not limited by the wireless communication component provided by the wireless network communication module.

The short-range wireless communication module is configured to include a short-range wireless communication module that connects to a communication session by using a radio frequency signal as a communication medium within a predetermined distance, and according to ISO 180000 series standards, the short-range wireless communication module may preferably include at least one of RFID communication, Bluetooth communication, Wi-Fi communication, and public wireless communication. In addition, the short-range wireless communication module may be integrated with the wireless network communication module.

The smart phone configured as described above is referred to a terminal capable of performing wireless communication, and other than the smart phone, any device may be applicable as long as the device is a terminal capable of transmitting and receiving data through a network including the Internet. That is, the smart phone may include at least one or more of a notebook PC, and a tablet PC, which have a function of transmitting a short message and a function of connecting to a network, in addition to a mobile terminal capable of being carried and moved.

The preferred exemplary embodiment of the mobile device for measuring radon in groundwater according to the present invention has been described above, but is not limited thereto, and it is possible to embody the present invention with various modifications within the scope of the claims, the detailed description of the present invention, and the accompanying drawings, and these embodiments also belong to the present invention.

INDUSTRIAL APPLICABILITY

The present invention is widely applicable in a mobile device for measuring radon in groundwater.

The invention claimed is:

1. A mobile device for measuring radon in groundwater, the mobile device comprising:
   a main body provided to be movable by a user and constituting an overall body;
   a groundwater sample chamber provided inside and outside the main body and storing a water sample collected from the groundwater;
   an air pump provided inside the main body, and configured to inject air into the water sample stored in the groundwater sample chamber at a constant pressure, and generating air bubbles;
   a buffer chamber provided inside the main body and configured to temporarily store the air bubbled by the air pump;
   a radon measurement part provided inside the main body, and configured to suction the air temporarily stored in the buffer chamber, detect in real time alpha particles present in the buffer chamber, output a predetermined alpha particle detection signal, count for a measurement time preset based on the output alpha particle detection signal, and calculate a radon concentration measurement value;

a display provided to be exposed to an outer surface of the main body and configured to display the radon concentration measurement value calculated from the radon measurement part on a display screen; and a control part provided inside the main body, and configured to control an operation of the air pump, the buffer chamber, and the radon measurement part so that the air bubbled by the air pump is moved to the radon measurement part via the buffer chamber, and configured to control an operation of the display so as to quantify the radon concentration measurement value calculated from the radon measurement part and display the radon concentration measurement value on the display screen.

2. The mobile device of claim 1, further comprising:
a communication part configured to wirelessly transmit a current radon concentration measurement value calculated from the radon measurement part, wherein the control part controls an operation of the communication part so that the current radon concentration measurement value calculated from the radon measurement part is transmitted to an external terminal in real time.

3. The mobile device of claim 2, wherein the external terminal receives the current radon concentration measurement value transmitted in real time from the communication part through a specific pre-installed application service, and displays the current radon concentration measurement value on the display screen so as to allow the user to visually check, in real time, the current radon concentration measurement on the basis of the received current radon concentration measurement value.

4. The mobile device of claim 3, wherein the external terminal collects the current radon concentration measurement value, transmitted in real time from the radon measurement part during a preset measurement period, through the pre-installed specific application services, calculates and quantifies an average value of the collected radon concentration measurement values, and displays the average value on the display screen.

5. The mobile device of claim 4, wherein the external terminal converts the current radon concentration measurement value transmitted in real time from the radon measurement part and/or a quantified radon concentration average value through the pre-installed specific application services into a database (DB) for each groundwater sample so as to be stored and managed therein.

6. The mobile device of claim 4, wherein, through the pre-installed specific application services, the external terminal generates a preset warning message of a radon risk according to the current radon concentration measurement value and/or a quantified radon concentration average value and displays the preset warning message on the display screen, when the corresponding current radon concentration measurement value transmitted in real time from the radon measurement part and/or the quantified radon concentration average value exceed a preset risk threshold value of radon concentration.

7. The mobile device of claim 2, wherein the external terminal collects the current radon concentration measurement value, transmitted in real time from the radon measurement part during a preset measurement period, through the pre-installed specific application services, calculates and quantifies an average value of the collected radon concentration measurement values, and displays the average value on the display screen.

8. The mobile device of claim 7, wherein the external terminal converts the current radon concentration measurement value transmitted in real time from the radon measurement part and/or a quantified radon concentration average value through the pre-installed specific application services into a database (DB) for each groundwater sample so as to be stored and managed therein.

9. The mobile device of claim 7, wherein, through the pre-installed specific application services, the external terminal generates a preset warning message of a radon risk according to the current radon concentration measurement value and/or a quantified radon concentration average value and displays the preset warning message on the display screen, when the corresponding current radon concentration measurement value transmitted in real time from the radon measurement part and/or the quantified radon concentration average value exceed a preset risk threshold value of radon concentration.

10. The mobile device of claim 1, wherein the control part collects the current radon concentration measurement value transmitted in real time from the radon measurement part during the preset measurement period, calculates and quantifies an average value of the collected radon concentration measurement values, and controls the operation of the display so as to display the average value on the display screen.

11. The mobile device of claim 10, further comprising:
a storage configured to store the current radon concentration measurement value transmitted in real time from the radon measurement part and a quantified radon concentration average value, wherein the control part controls to convert the current radon concentration measurement value transmitted in real time from the radon measurement part and/or the quantified radon concentration average value into a database (DB) for each groundwater sample, so as to be stored and managed in the storage.

12. The mobile device of claim 1, wherein the buffer chamber is provided with a plurality of partitions installed therein for increasing an inner surface area in order to maintain moisture in the air bubbled by the air pump at a constant humidity.

13. The mobile device of claim 1, wherein the radon measurement part comprises at least one radon measurement sensor using an ionization chamber method, and an internal capacity of the buffer chamber is provided in a range of 1.5 to 2 times larger than an internal capacity of the ionization chamber provided in the radon measuring part.

* * * * *